(12) United States Patent
Koschmieder et al.

(10) Patent No.: US 7,380,943 B2
(45) Date of Patent: Jun. 3, 2008

(54) METHOD AND ARRANGEMENT FOR DETERMINING THE ADJUSTED MAGNIFICATION STEP IN OPHTHALMOLOGIC INSTRUMENTS, PARTICULARLY SLIT LAMPS

(75) Inventors: Ingo Koschmieder, Jena (DE); Egon Luther, Cospeda (DE); Bernd Spruck, Moegglingen (DE)

(73) Assignee: Carl Zeiss Jena GmbH, Jena (DE)

( * ) Notice: Subject to any disclaimer, the term of this patent is extended or adjusted under 35 U.S.C. 154(b) by 560 days.

(21) Appl. No.: 10/856,623

(22) Filed: May 27, 2004

(65) Prior Publication Data

US 2004/0252279 A1 Dec. 16, 2004

(30) Foreign Application Priority Data

May 28, 2003 (DE) ................................ 103 24 238

(51) Int. Cl.
*A61B 3/00* (2006.01)
(52) U.S. Cl. ..................................... 351/246
(58) Field of Classification Search ......... 351/245–246
See application file for complete search history.

(56) References Cited

U.S. PATENT DOCUMENTS 6,575,571 B2 * 6/2003 Shibata ....................... 351/206

FOREIGN PATENT DOCUMENTS

DE 0 453 239 10/1991
JP 02-191909 7/1990

\* cited by examiner

*Primary Examiner*—Alicia M Harrington
(74) *Attorney, Agent, or Firm*—Reed Smith LLP

(57) ABSTRACT

The present invention is directed to a method and an arrangement for automatic detection, documentation and reproduction of the adjusted magnification. The magnification steps are read off at the rotational axis of the magnification changer, monitored by a control unit and stored for reproducing the magnification setting. For this purpose, a cylinder is arranged on the rotational axis of the magnification changer, this cylinder having a quantity of magnets with radially oriented magnetic fields which divide the cylinder into segments. An arrangement of sensors which are fixedly connected to the housing is located opposite from these magnets for detection of their magnetic fields. The quantity and arrangement of sensors correspond to the quantity and arrangement of magnets. The solution supports a comprehensive computer-assisted control of the instruments and offers the possibility of defined standardized sequences. Further, it is possible to let the magnification step be adapted to the observation task automatically or to ensure remote control capability through voice control.

11 Claims, 3 Drawing Sheets

4   5   2   1   3   6   7

METHOD AND ARRANGEMENT FOR DETERMINING THE ADJUSTED MAGNIFICATION STEP IN OPHTHALMOLOGIC INSTRUMENTS, PARTICULARLY SLIT LAMPS

CROSS-REFERENCE TO RELATED APPLICATIONS

This application claims priority of German Application No. 103 24 238.4, filed May 28, 2003, the complete disclosure of which is hereby incorporated by reference.

BACKGROUND OF THE INVENTION a) Field of the Invention

The present invention is directed to a method and an arrangement for automatic detection, documentation and reproduction of the adjusted magnification in ophthalmologic instruments, particularly slit lamps. This is accomplished by means of a device which is arranged at the magnification changer and which supplies an electronically readable code depending on the optical component that is swiveled in.

b) Description of the Related Art

The slit lamp is one of the most common ophthalmologic instruments for examination of the eyes. It is particularly important for the ophthalmologist that an appropriate magnification can be adjusted depending on the area to be examined. In the known prior art, this is carried out by turning a knob which allows the corresponding magnification to be adjusted in individual steps by swiveling different optical components into the beam path. When the data gathered during an eye examination must be processed further, it is of particular concern that the adjusted magnification be documented. Generally, in ophthalmologic instruments an imaging scale is associated with (calibrated to) a determined magnification by a comparison scale. This magnification setting associated with the calibration value is reproducible by means of a scale with or without click-stop or locking positions. The adjustment is read off instantaneously at the rotating knob and is correspondingly noted.

A control device for a microscope by which the magnification as well as the focusing and illumination can be adjusted by means of electric drives is known from JP 02 191 909. As a rule, a data storage in which the required settings are stored is accessed by means of various switches.

EP 0 453 239 also describes an optical microscope with variable magnification in which the magnification is adjustable by means of a motor. In this case, starting from a desired image section, the maximum magnification is calculated and the corresponding lens system is introduced into the beam path by means of a motor. Among other things, the illumination intensity is adapted to the magnification simultaneously.

These solutions have the disadvantage that the adjustment of magnification is always coupled with the adjustment of focus and illumination. For ophthalmologic instruments, particularly slit lamps, this is not flexible enough since changes in magnification and/or illumination (intensity, color, pattern, etc.) are sometimes necessary during the examination.

OBJECT AND SUMMARY OF THE INVENTION

It is the primary object of the present invention to develop an automatically detectable, documentable and reproducible adjustment of the magnification in ophthalmologic instruments, particularly slit lamps.

According to the invention, this object is met in a method for determining the adjusted magnification step in opthalmologic instruments, particularly slit lamps comprising reading off magnification steps at the rotational axis of a magnification changer, monitoring said steps by a control unit and storing the magnification setting for reproduction.

An arrangement for determining the adjusted magnification step in opthalmological instruments, particularly slit lamps, is also described.

The proposed technical solution is also applicable to other ophthalmologic instruments besides slit lamps. By combining ophthalmologic instruments with digital technology for image acquisition, image processing and image storage, it possible to make use of PC techniques not only for data storage but also for controlling the instruments. Accordingly, in addition to saving time in examinations, greater operating convenience and a greater flexibility of the instruments can also be achieved.

In the following, the invention will be described with reference to an embodiment example.

DESCRIPTION OF THE PREFERRED EMBODIMENTS

In the method for determining the adjusted magnification step in ophthalmologic instruments, particularly slit lamps, the magnification steps are read off at the rotating shaft or rotational axis of the magnification changer, monitored by a control unit and stored for reproduction of the magnification setting. The magnification steps are preferably read off electrically, magnetically, optically, acoustically or mechanically. When the rotational axis of the magnification changer has locking positions, the magnification steps are read off exactly when the magnification changer is located in these locking positions.

The adjusted, read off magnification steps are introduced into the observation beam path so that they are visible in the eyepiece and/or on a monitor. A stored or selected magnification step can be produced again by an adjusting drive.

Figure 1:
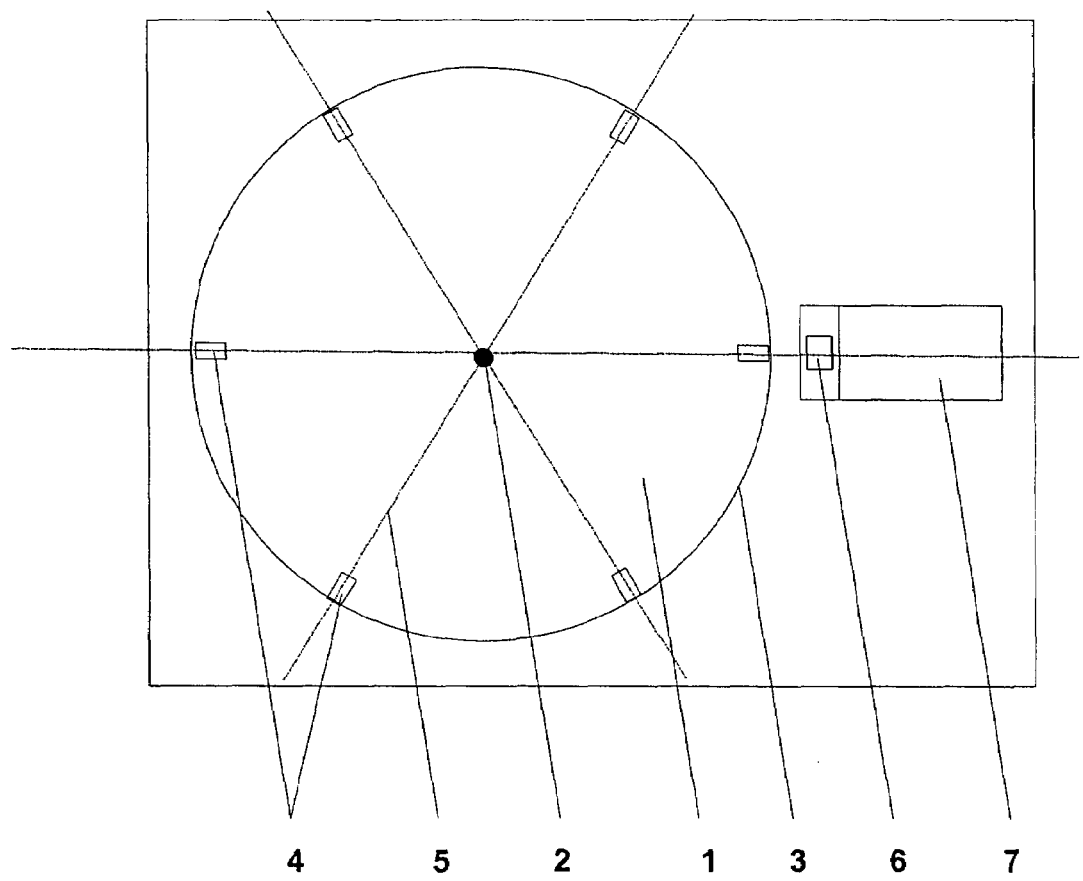
FIG. 1 shows a cylinder with magnets for six magnification steps corresponding to a 60-degree graduation.

A special embodiment example for an arrangement for determining the adjusted magnification step in ophthalmologic instruments, particularly slit lamps, is shown in FIG. 1. In this case, the magnification step is read off magnetically. For this purpose, a cylinder 1 of nonmagnetic material, e.g., aluminum, having on or in its jacket surface 3, a quantity of magnets 4 with radially oriented magnetic fields is arranged on the rotational axis of the magnification changer. These magnets 4 which are likewise cylindrical, for example, are preferably embedded in the jacket surface 3 of the cylinder 1 so that a pole terminates at the jacket surface 3. The magnets 4 are arranged so as to be equidistant in a line in the jacket surface 3 in such a way that the cylinder 1 is divided into equal segments. An arrangement of sensors 6 which are fixedly connected to the housing is located opposite from these magnets 4 for detection of their magnetic fields. The quantity of sensors 6, which are likewise arranged on a line, corresponds to the quantity of magnets located on a segment boundary 5.

Figure 2:
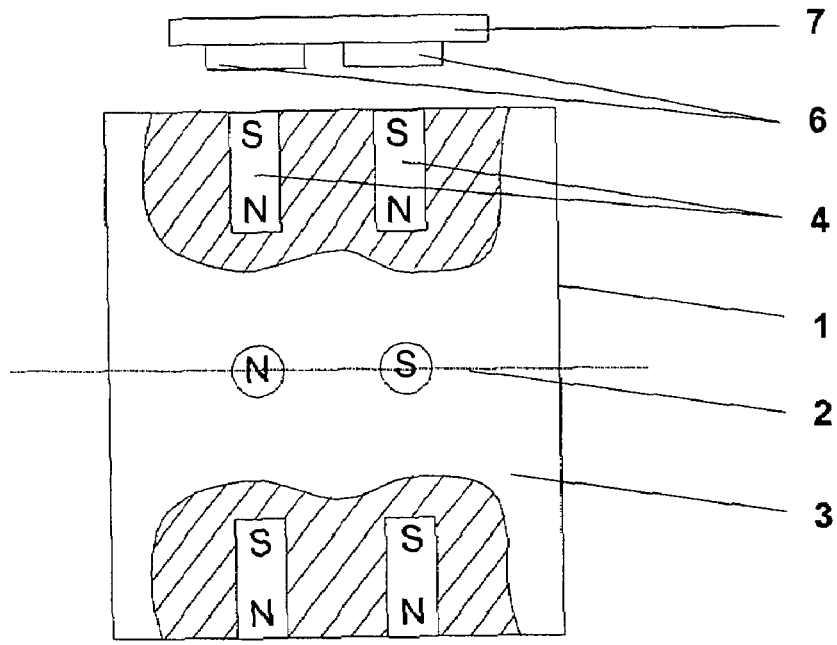
FIG. 2 shows a view in partial section through a cylinder with magnets for four magnification steps corresponding to a 90-degree graduation.
Figure 3:
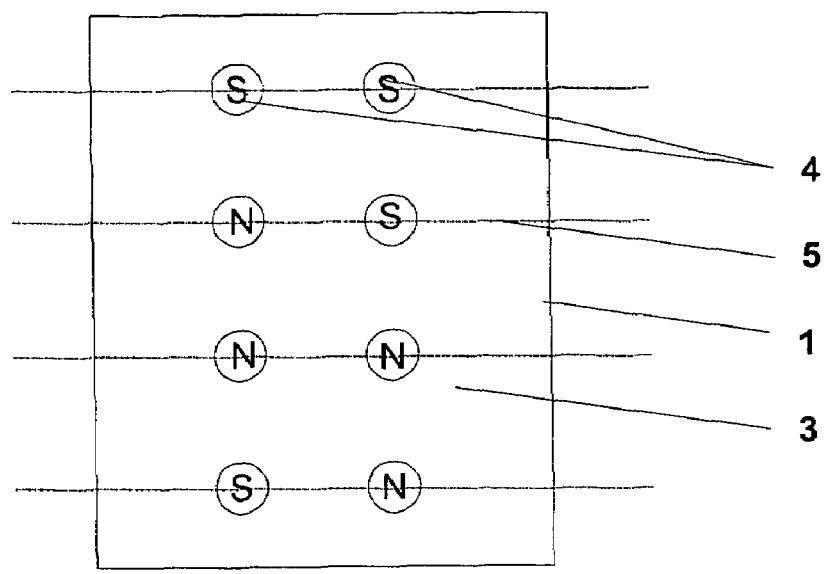
FIG. 3 shows the jacket surface of the cylinder from FIG. 2.

FIG. 2 shows a simple arrangement in which two magnets 4 whose magnetic fields do not influence one another are arranged on the lines constituting the segment boundaries 5. The magnets 4 are oriented in such a way that the pole arrangement of the associated magnets 4 located on a segment boundary 5 occurs only once on the jacket surface 3 in this combination and arrangement. The cylinder 1 can accordingly be divided into as many as four segments of equal size. In this connection, FIG. 3 shows the jacket surface 3 of the cylinder 1 from FIG. 2 with four pairs of magnets 4. However, only four magnification steps can be read off with this arrangement. Since ophthalmologic instruments generally have more than four magnification steps, arrangements with more than two magnets 4 on every segment boundary 5 are practical.

FIG. 1 shows a cylinder 1 which has a 60-degree graduation and is accordingly provided for reading off six magnification steps. Three magnets 4 are arranged in a line on each segment boundary 5. The magnets 4 which do not influence one another are again oriented in such a way that the pole arrangement of the associated magnets 4 located on a segment boundary 5 occurs only once in this combination and arrangement on the jacket surface 3. Consequently, three sensors arranged next to one another are positioned opposite the magnets 4. The sensors 6 are Hall sensors which detect the fields of the magnets 4 and convert them into a corresponding electric signal. The Hall sensors 6 are embodiment forms in which a defined magnetic polarity, for example, the south pole, on the one hand and a defined magnetic field strength on the other hand is awaited before triggering a switching signal. The Hall sensors 6 are preferably arranged on a shared printed circuit board 7 with the corresponding electric circuits for evaluating the generated switching signals.

Accordingly, in the evaluation, a definite correlation between the optics presently swiveled in and the adjusted magnification is possible. The following table shows one possible correlation:

| Sensor A | Sensor B | Sensor C | Adjusted magnification step |
|----------|----------|----------|----------------------------|
| 0 | 0 | 1 | 5 |
| 0 | 1 | 0 | 8 |
| 0 | 1 | 1 | 12 |
| 1 | 0 | 0 | 20 |
| 1 | 0 | 1 | 32 |

The Hall sensors 6 (A to C) deliver a switching signal (corresponds to 1) when they detect a south pole of corresponding field strength. Otherwise, no switching signal (0) is emitted. The corresponding field strength is only achieved when the south pole and the sensor are located exactly opposite from one another.

Figure 4:
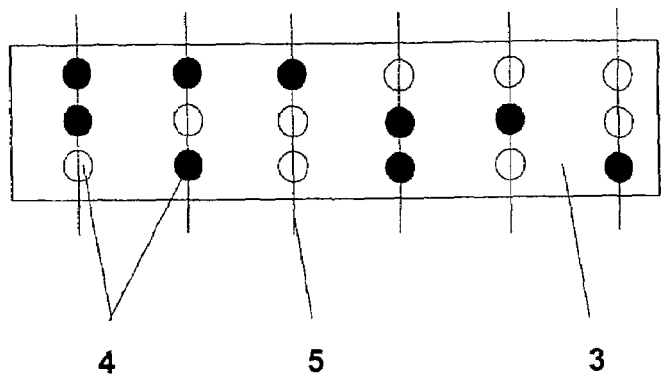
FIGS. 4a to c show possible magnet arrangements for a 60-degree graduation.
Figure 4:
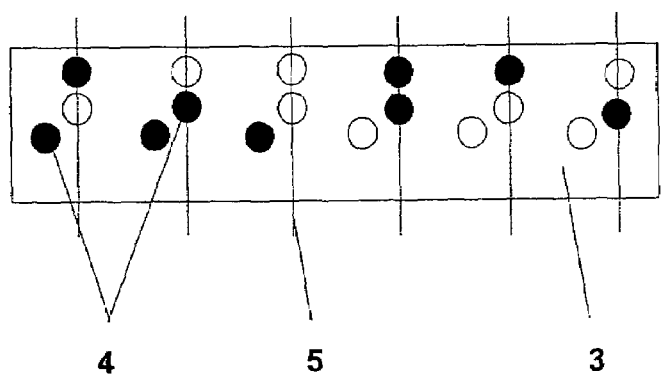
Figure 4:
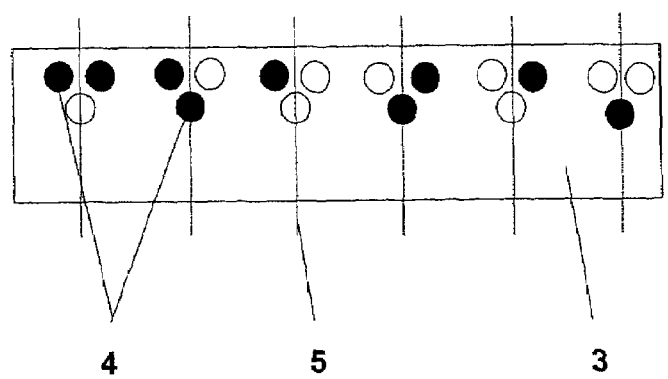

Since the Hall sensors 6 detect only the south pole, for example, the magnets 4 whose north pole faces radially outward can simply be omitted. The corresponding position in the geometric arrangement of the magnets 4 remains empty. In any case, there are different possible geometric arrangements for the arrangement of magnets 4 on the segment boundaries 5. In case of space problems, compact arrangements are conceivable. FIGS. 4a to 4c show possible arrangements of the magnets 4. The magnets 4 with the south pole oriented radially outward are identified by solid black circles and the magnets 4 with the north pole oriented radially outward are identified by white circles. As was already mentioned, the latter can also be omitted under certain conditions. Further, graduations of the cylinder 1 in segments of different sizes are also conceivable. The only condition to be ensured is that the magnets 4 may not influence one another. In contrast to the arrangements shown in FIGS. 4a and 4b, the arrangement according to FIG. 4c functions only with simultaneous detection of the locking positions. Otherwise, an erroneous detection would be initiated because the magnets 4 are arranged one behind the other in the direction of rotation in this instance. This applies to the determination of the adjusted magnification as well as to the automatic adjustment of a stored or desired magnification. In this magnet arrangement, the magnetic fields can be exactly detected by the Hall sensors and the corresponding magnification step determined only when the magnification changer is in a locking position and the magnets are located exactly opposite from the sensors. For this purpose, it is necessary, in addition, to detect when the locking positions are reached.

A stored or selected magnification step can be produced again by an adjusting drive. Accordingly, it is possible for the observer to carry out specific presettings of the magnification step relating to the intended purpose of the examination or to a pre-examination. The adjusting drive can be controlled in a variety of ways, e.g., acoustically, by pressing a button, by programming or as a function of the examination to be initiated.

Depending on the setting of the adjusted magnification step in ophthalmologic instruments, particularly slit lamps, other instrument parameters such as the size of the viewing field, depth of focus, illumination intensity and dosage, geometry of the illumination field, illumination spectrum, etc. can be controlled.

The method and the arrangement according to the invention for determining the adjusted magnification step in ophthalmologic instruments, particularly slit lamps, provides a solution which supports a comprehensive computer-assisted control of the instruments.

The solution offers the possibility of defined standardized sequences by means of an automatic magnification change resulting in documentation which can easily be compared. Further, it is possible to adapt the magnification step to the observation task automatically. However, variants in which remote control capability can be ensured through voice control are also possible.

While the foregoing description and drawings represent the present invention, it will be obvious to those skilled in the art that various changes may be made therein without departing from the true spirit and scope of the present invention.

What is claimed is:

1. A method for determining the adjusted magnification step in ophthalmologic instruments, particularly slit lamps, comprising:
   reading off magnification steps at the rotational axis of a magnification changer, monitoring said steps by a control unit; and
   storing the magnification setting for reproduction, and wherein the magnification steps are read off by Hall sensors at a cylinder arranged on the rotational axis of the magnification changer, which cylinder has for this purpose on or in its jacket surface magnets with radially oriented magnetic fields which divide the cylinder into segments, at least two magnets being provided at the segment boundaries in a defined geometric arrangement and oriented in such a way that the pole arrangement of the associated magnets located at a segment boundary occurs only once in this combination and arrangement on or in the jacket surface of the cylinder, and wherein an identical quantity of sensors is located opposite from these magnet arrangements in the same geometric arrangement for reading off the magnification steps, and the read off magnification steps are monitored and stored by a control unit.

2. The method according to claim 1, wherein no magnets with outwardly directed north pole or no magnets with outwardly directed south pole are provided.

3. The arrangement according to claim 2, wherein at least two magnets are arranged on the segment boundaries, the magnetic fields of the magnets do not influence one another and are oriented in such a way that the pole arrangement of the associated magnets located on a segment boundary occurs only once on or in the jacket surface in this combination and arrangement, and the cylinder is accordingly divided into as many as four segments.

4. The arrangement according to claim 2, wherein three magnets are arranged on the segment boundaries, the magnetic fields of the magnets do not influence one another and are oriented in such a way that the pole arrangement of the associated magnets located on a segment boundary occurs only once on or in the jacket surface in this combination and arrangement, and the cylinder is accordingly divided into as many as eight segments.

5. The method according to claim 1, wherein a stored or selected magnification step can be produced again by an adjusting drive.

6. An arrangement for determining the adjusted magnification step in ophthalmologic instruments, particularly slit lamps, comprising:

for purposes of magnetically reading off the magnification step, a cylinder of nonmagnetic material being provided on the rotational axis of the magnification changer and having, on or in a jacket surface, a quantity of magnets with radially oriented magnetic fields which divide the cylinder into segments;

at least two magnets being provided at the segment boundaries in a defined geometric arrangement and oriented in such a way that the pole arrangement of the associated magnets located at a segment boundary occurs only once in this combination and arrangement on or in the jacket surface of the cylinder;

an identical quantity of sensors being located opposite from said magnet arrangements in the same geometric arrangement; and a control unit being provided for monitoring the read off magnification steps and for storing said magnification steps.

7. The arrangement according to claim 6, wherein the quantity and the geometric arrangement of the sensors correspond to the quantity and geometric arrangement of the magnets located on a segment boundary.

8. The arrangement according to claim 6, wherein Hall sensors are used as sensors.

9. The arrangement according to claim 6, wherein the magnets located on a segment boundary are located opposite from the sensors respectively in one of the locking positions of the magnification changer.

10. The arrangement according to claim 6, wherein a stored or selected magnification step can be produced again by adjusting drives.

11. The arrangement according to claim 6, wherein the magnets with outwardly directed north pole or the magnets with outwardly directed south pole can be omitted from the arrangement.

\* \* \* \* \*